US008915838B2

(12) United States Patent
Ozaki

(10) Patent No.: US 8,915,838 B2
(45) Date of Patent: Dec. 23, 2014

(54) MEDICAL APPARATUS AND MEDICAL SYSTEM PROVIDED WITH THE SAME

(75) Inventor: Takashi Ozaki, Hachioji (JP)

(73) Assignee: Olympus Corporation, Tokyo (JP)

( * ) Notice: Subject to any disclaimer, the term of this patent is extended or adjusted under 35 U.S.C. 154(b) by 1591 days.

(21) Appl. No.: 12/184,823

(22) Filed: Aug. 1, 2008

(65) Prior Publication Data

US 2009/0043163 A1    Feb. 12, 2009

(30) Foreign Application Priority Data

Aug. 10, 2007    (JP) .................................. 2007-210002

(51) Int. Cl.
*A61B 1/04*    (2006.01)
*G06F 19/00*    (2011.01)

(52) U.S. Cl.
CPC .................................... *G06F 19/321* (2013.01)
USPC ......................................................... 600/118

(58) Field of Classification Search
CPC ........ A61B 19/56; A61B 6/566; A61B 8/565; A61B 5/0013
USPC ......................................................... 600/118
See application file for complete search history.

(56) References Cited

U.S. PATENT DOCUMENTS

| | | | |
|---|---|---|---|
| 4,827,908 A * | 5/1989 | Matsuo .......................... | 600/109 |
| 6,351,547 B1 | 2/2002 | Johnson et al. | |
| 6,436,032 B1 * | 8/2002 | Eto et al. ........................ | 600/117 |
| 6,902,529 B2 * | 6/2005 | Onishi et al. ................... | 600/118 |
| 2003/0097042 A1 * | 5/2003 | Eino .............................. | 600/118 |
| 2004/0107113 A1 * | 6/2004 | Araki ............................... | 705/1 |
| 2004/0122703 A1 * | 6/2004 | Walker et al. ..................... | 705/2 |
| 2004/0141661 A1 | 7/2004 | Hanna et al. | |
| 2004/0243448 A1 * | 12/2004 | Shoji et al. ......................... | 705/3 |
| 2006/0048209 A1 * | 3/2006 | Shelest et al. ..................... | 726/1 |
| 2006/0055793 A1 * | 3/2006 | Adler et al. ............. | 348/211.99 |
| 2006/0106284 A1 * | 5/2006 | Shouji et al. .................. | 600/118 |
| 2006/0197830 A1 * | 9/2006 | Takeuchi et al. ............... | 348/65 |

(Continued)

FOREIGN PATENT DOCUMENTS

| | | |
|---|---|---|
| CN | 1827034 A | 9/2006 |
| JP | 2005-081083 | 3/2005 |

(Continued)

OTHER PUBLICATIONS

Extended European Search Report dated Feb. 9, 2010.

(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

In the present invention, an endoscope apparatus has an identification unit which identifies the classification on the basis of scope ID information of an endoscopic scope, a storage unit which stores information regarding processing to be executed according to the classification of the endoscopic scope (a first SOP), and a control unit which reads a second SOP corresponding to the classification from the first SOP stored in the storage section on the basis of the result of the identification by the identification unit and sets the second SOP, and which, in the case where the information corresponding to the classification does not exist, performs switching so that predetermined information (a third SOP) is read from the first SOP stored in the storage unit and sets the predetermined information.

6 Claims, 6 Drawing Sheets

(56) References Cited

U.S. PATENT DOCUMENTS

| | | |
|---|---|---|
| 2007/0038023 A1* | 2/2007 | Uchimura et al. ............ 600/109 |
| 2007/0103725 A1* | 5/2007 | Kawahara et al. ........... 358/1.15 |
| 2007/0237375 A1* | 10/2007 | Yamagishi et al. ........... 382/128 |
| 2008/0242983 A1* | 10/2008 | Hibi .............................. 600/441 |
| 2008/0249361 A1* | 10/2008 | Okuno .......................... 600/118 |
| 2009/0124855 A1* | 5/2009 | Urakawa ....................... 600/109 |
| 2009/0187550 A1* | 7/2009 | Mowatt et al. ................... 707/5 |

FOREIGN PATENT DOCUMENTS

| | | |
|---|---|---|
| JP | 2005-204741 A | 8/2005 |
| JP | 2005-237420 A | 9/2005 |
| JP | 2007-144151 A | 6/2007 |

OTHER PUBLICATIONS

Chinese Official Action dated Jan. 22, 2010.

* cited by examiner

MEDICAL APPARATUS AND MEDICAL SYSTEM PROVIDED WITH THE SAME

This application claims benefit of Japanese Application No. 2007-210002 filed in Japan on Aug. 10, 2007, the contents of which are incorporated herein by this reference.

BACKGROUND OF THE INVENTION

1. Field of the Invention

The present invention relates to a medical apparatus capable of efficiently making various settings accompanying communication of image data, and a medical system provided with the medical apparatus.

2. Description of the Related Art

Recently, the DICOM (Digital Imaging and Communications in Medicine) standard has been attracting attention, which is the standard specifications for medical images and communication to enable exchange of imaging test information about patients and transmission of image data by mutually connecting digital image apparatuses of different manufacturers (multi-vendor) and different types (multi-modality) via a network or an image storage medium inside and outside a hospital.

In the DICOM standard, specification is made on a wide range of items such as tests among multi-vendors or multi-modality apparatuses; management of reservation data before giving medical treatment; transfer of picked-up image data and storage of the image data to a medical server; and search for image data from a terminal, storage of the image data into a storage medium and output of the image data to a printer.

As the digital image apparatuses, there are an image generation apparatus (for example, a medical apparatuses such as an endoscope apparatus, CT (Computed Tomography) apparatus, an MRI (magnetic resonance imaging) apparatus, an ultrasound imaging apparatus, a nuclear medicine imaging apparatus, a CR apparatus, a film digitizer, and the like), an image storage apparatus (such as a medical server), image display/processing/diagnostic apparatuses (such as a CORT, a workstation and the like), an image printing apparatus (such as a laser imager), and the like. A medical system is constructed having such apparatuses.

It is expected that, by the DICOM standard realizing meaningful mutual connection among the image apparatuses in accordance with the purpose of medical treatment, the problems of the conventional image-based medical treatment system in which films are positioned as the center thereof (such as lack of storage space, loss of films and slow delivery) can be conquered, and newly added value of image-based medical treatment (such as digital image processing, computer-aided diagnosis and overall diagnostic imaging) can be obtained.

In the DICOM standard, various functions in communication are referred to as services. The services are classified in fields, such as "image search", "test information search" and "image printing", and defined as service classes. As examples of the service class, "Verification service" for network interconnection, "Storage service" for storing image information, "Query/Retrieve service" for searching for and acquiring a test image from a server, and the like are given.

A service class is configured by some SOPs (Service Object Pairs), and an SOP is defined by a set of one IOD (Information Object Definition) and one or more DIMSE's (DICOM Message Service Elements).

When DICOM communication is performed in a system provided with digital image apparatuses compatible with the DICOM standard, it is necessary that there exist an SCU (Service Class User) on the side of an apparatus having a DICOM application for performing a request for a service and the like (corresponding to a client in a client-server system) and an SCP (Service Class Provider) on the side of an apparatus having a DICOM application for performing an operation requested by the SCU (corresponding to a medical server), and one-for-one communication is necessarily performed in which one is an SCU and the other is an SCP.

As an example of a conventional technique related to apparatuses compatible to the DICOM standard, there is, for example, a diagnostic imaging apparatus described in Japanese Patent Application Laid-Open Publication No. 2005-81083.

Japanese Patent Application Laid-Open Publication No. 2005-81083 discloses a technique related to a diagnostic imaging apparatus which makes it possible to supply medical information which is not supported by the general DICOM standard to a medical viewer as a DICOM file together with image data and display the information, by being provided with image data generation means, display software storage means for storing display software for displaying medical image data and medical information, DICOM file generation means for generating a DICOM file, and DICOM file supply means for supplying the generated DICOM file to the medical viewer via a network.

The digital image apparatuses compatible with the DICOM standard include, for example, medical apparatuses such as an endoscope apparatus. Such a medical apparatus can be used not only for ordinary visible-light tests but also for special-light tests and ultrasound tests. In order to perform such various tests, endoscopic scopes, which are testing apparatuses to be used according to the tests, can be freely attached to and detached from the medical apparatus.

SUMMARY OF THE INVENTION

The medical apparatus of the present invention is configured to be provided with: identification means for identifying the classification of a medical testing apparatus; storage means for storing information regarding processing to be executed according to the classification of the medical testing apparatus; and control means for reading, on the basis of the classification of the medical testing apparatus obtained by the identification means, information corresponding to the classification from the information stored in the storage means and setting the information, and, in the case where the information corresponding to the classification does not exist, performing switching so that predetermined information is read from the information stored in the storage means and set the information.

Furthermore, the medical system of the present invention is configured to be provided with:

a medical apparatus provided with:

a medial testing apparatus;

identification means for identifying the classification of the medical testing apparatus;

storage means for storing information regarding processing to be executed according to the classification of the medical testing apparatus; and control means for reading, on the basis of the classification of the medical testing apparatus obtained by the identification means, information corresponding to the classification from the information stored in the storage means and setting the information, and, in the case where the information corresponding to the classification does not exist, performing switching so that predetermined information is read from the information stored in the storage means and set the predetermined information; and a medical server capable of sending and receiving image data to and from the medical apparatus by connecting the medical apparatus via a network.

The characteristics and benefits of the present invention will be sufficiently apparent from the following description.

DETAILED DESCRIPTION OF THE PREFERRED EMBODIMENTS

<First Embodiment>

According to the DICOM standard, one-for-one communication is performed between an SCU and an SCP. Therefore, for example, in the case of a medical system in which a medical apparatus is an SCU and a medical server is an SCP, the medical apparatus outputs image data on the basis of an SOP set in advance.

Therefore, in a medical apparatus compatible with the conventional DICOM standard, all test images must be visible-light test images based on the SOP set in advance, that is, there is a problem that it is not possible to, when an endoscopic scope for special-light tests or an endoscopic scope for ultrasound tests is attached, switch to and set an SOP appropriate for the test.

For example, it is disclosed in Japanese Patent Laid-Open No. 2005-81083 described before that the diagnostic imaging apparatus is provided with the display software storage means, the DICOM file generation means for generating a DICOM file and the DICOM file supply means so as to supply medical information which is not supported by the general DICOM standard, to the medical viewer as a DICOM file together with image data. However, nothing is disclosed or suggested about, when an endoscopic scope for special-light tests or an endoscopic scope for ultrasound tests, which is a modality, is attached to a medical apparatus compatible with the DICOM standard, switching to an SOP appropriate for the test and setting the SOP.

The embodiment described below has been made in consideration of the above situation, and its object is to provide a medical apparatus capable of outputting optimum image data compatible with the DICOM standard by selecting settings to be applied to test processing by a testing apparatus from setting information stored in advance on the basis of the result of identification of the testing apparatus and applying the settings, and a medical system having the medical apparatus.

Figure 1:
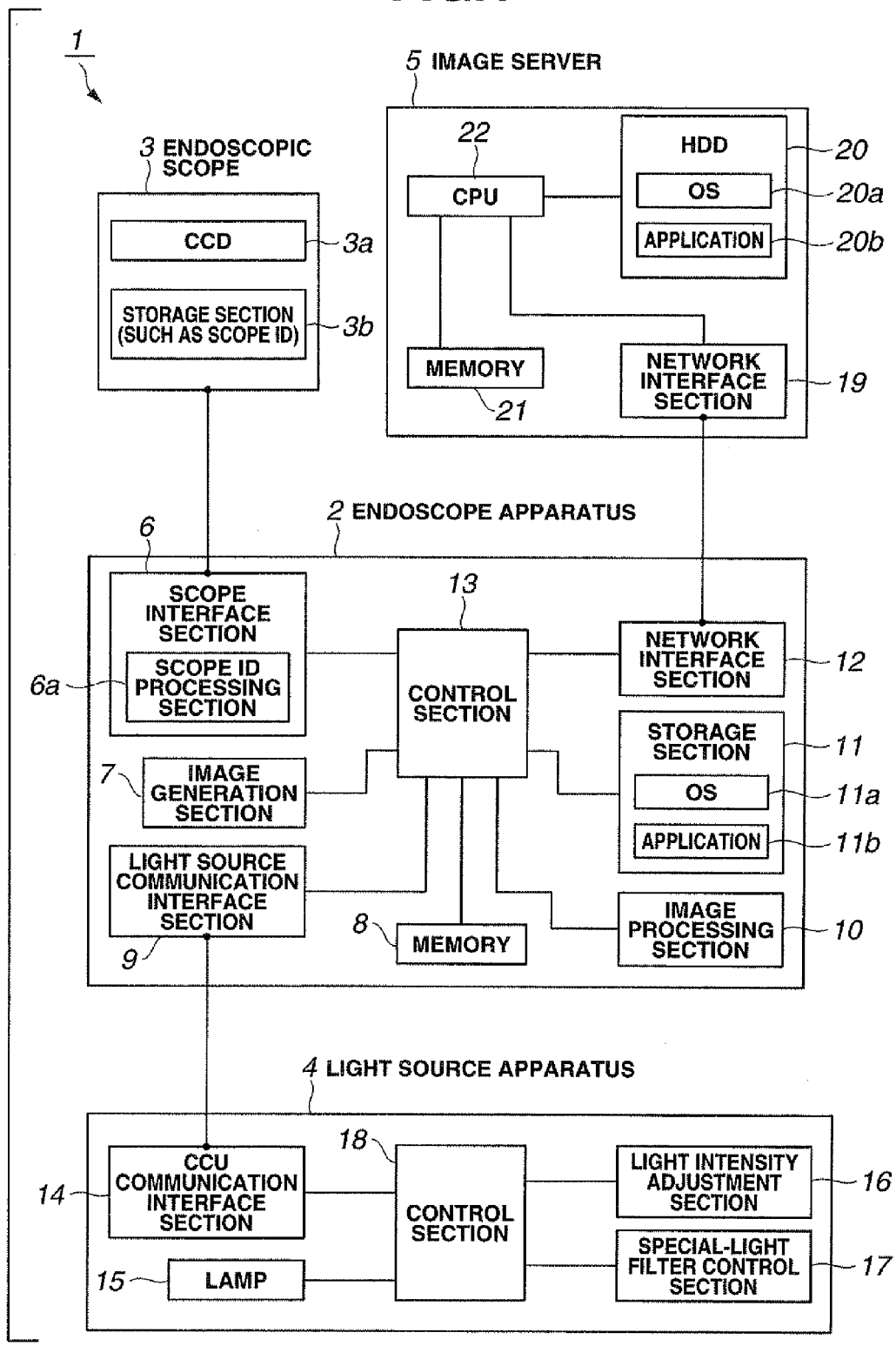
FIG. 1 is a block diagram showing the entire configuration of a medical system provided with a medial apparatus, according to a first embodiment.

As shown in FIG. 1, a medical system 1 of the present embodiment is configured to have an endoscope apparatus 2 compatible with the DICOM standard which constitutes a medical apparatus, an endoscopic scope 3 constituting a testing apparatus which can be attachably and detachably connected the endoscope apparatus 2 and a light source apparatus 4, the light source apparatus 4 connected to the endoscope apparatus 2 and the endoscopic scope 3 to generate illumination light required when a test by the endoscopic scope 3 is performed, and an image server 5 which is a medical server connected to the endoscope apparatus 2 via a network. The endoscope apparatus 2 and the light source apparatus 4 constitute the testing apparatus.

The endoscopic scope 3 has a solid-state image sensing device (CCD) 3a for picking up an optical image of the subject which is provided, for example, inside the distal end portion of an insertion section, and a storage section 3b, such as an EPROM, in which identification information such as a scope ID indicating the type of the endoscopic scope 3 is stored.

Figure 3:
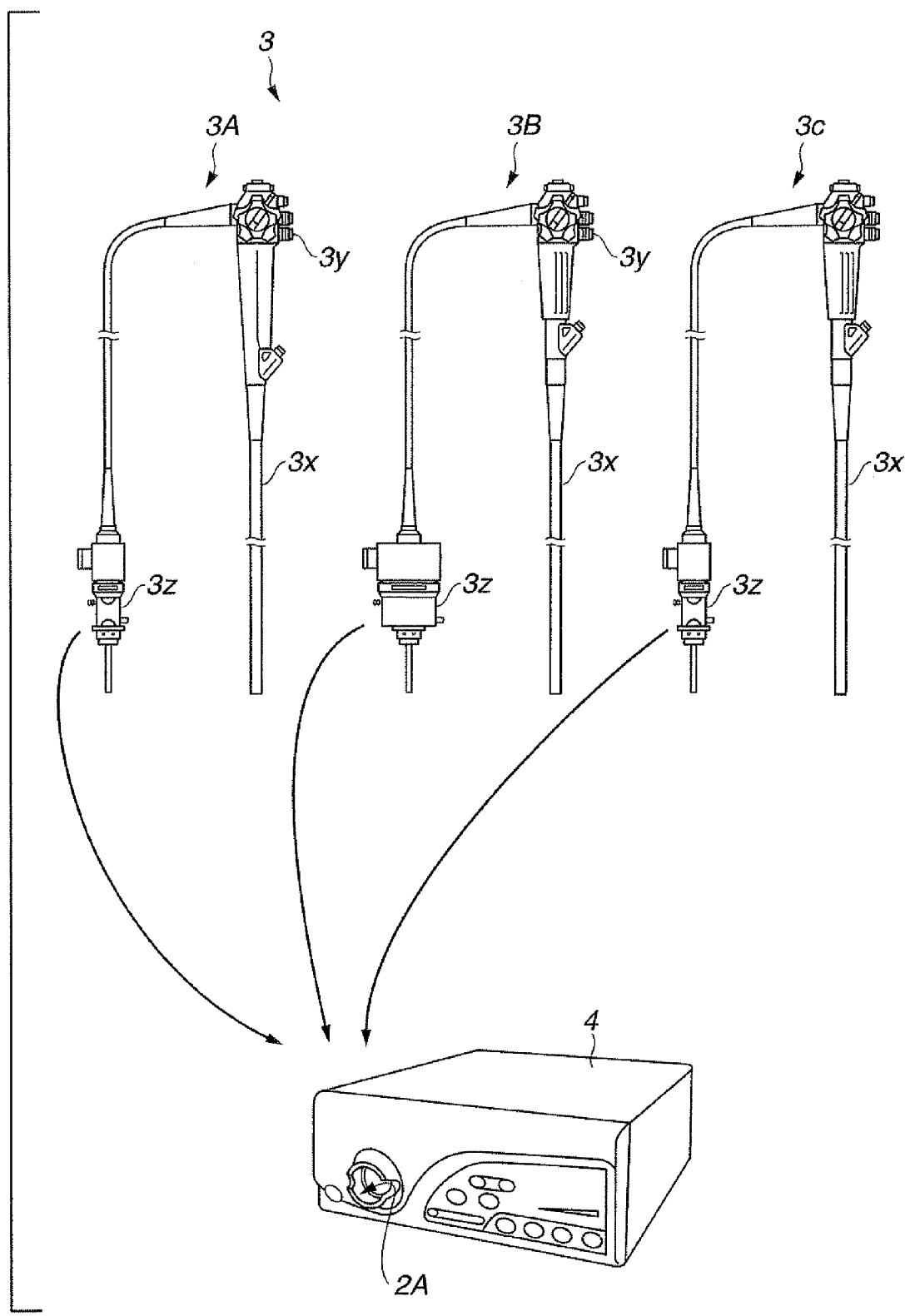
FIG. 3 is a diagram showing multiple types of endoscopic scopes which can be attached to and detached from the medical apparatus and a light source apparatus in FIG. 1.

As the endoscopic scope 3, there are, for example, a visible-light test endoscopic scope 3A for performing an ordinary visible-light test, an ultrasound test endoscopic scope 3B for performing an ultrasound test with the use of ultrasound waves, and a special-light test endoscopic scope 3C for performing a special-light test with the use of special light as shown in FIG. 3.

As is generally known, each of the endoscopic scopes 3A to 3C is configured to have an elongated and narrow insertion section 3x to be inserted into a body cavity, a grasping section 3y provided on the proximal end side of the insertion section 3x, and a connector section 3z which is provided on the proximal end side of a universal code and which is detachably attached to the endoscope apparatus 2. The endoscopic scopes 3A to 3C are well-known techniques and are not main parts of the present invention. Therefore, description of the specific configuration thereof is omitted.

Any endoscopic scope 3 among the endoscopic scopes 3A to 3C is selected according to the contents of a test. As shown in FIG. 3, by inserting the connector section 3z of the selected endoscopic scope 3 into a connector section 2A of the light source apparatus 4, the endoscopic scope 3 is connected to the light source apparatus 4. Furthermore, the endoscopic scope 3 is connected to the endoscope apparatus 2 via a scope cable not shown.

In this case, when the endoscopic scope 3 is connected to the light source apparatus 4 and the endoscope apparatus 2, the identification information, such as a scope ID, which is stored in the storage section 3b of the endoscopic scope 3 is taken in by a scope interface section 6 to be described later, which is in the endoscope apparatus 2, via the scope cable (not shown).

In the scope cable which connects the light source apparatus 4 and the endoscopic scope 3, a light guide cable for transmitting illumination light is provided. The light source apparatus 4 supplies the illumination light of the light source apparatus 4 to a light guide of the endoscopic scope 3 to illuminate a diseased part or the like in the body cavity of a patient in which the insertion section 3x of the endoscopic scope 3 is inserted.

Then, the endoscopic scope 3 picks up an optical image of the diseased part or the like obtained by an optical observation system (not shown) which is provided inside the distal end portion of the insertion section 3x, with the use of the CCD 3a provided inside the distal end portion of the insertion section 3x, and transmits the image pickup signal picked up to the endoscope apparatus 2 via the universal code.

Next the configuration of the light source apparatus 4 which supplies illumination light to the endoscopic scope 3 will be described. As shown in FIG. 1, the light source apparatus 4 is configured to have a CCU communication interface section 14 for performing communication with the endoscope apparatus 2, a lamp 15 which is a light source for generating illumination light, a light intensity adjustment section 16 which adjusts the light intensity of the lamp 15, a special-light filter control section 17 which controls driving of a special-light filter for generating special light when the special-light test endoscopic scope 3C is connected, and a control section 18 which controls the entire light source apparatus 4 including the above blocks (the CCU communication interface section 14, the lamp 15, the light intensity adjustment section 16 and the special-light filter control section 17).

The CCU communication interface section 14 is an interface for electrically connecting to a light source communication interface section 9 of the endoscope apparatus 2, which is to be described later, to perform communication. For example, when an operation of selecting a light source filter is performed, the CCU communication interface section 14 sends identification information such as the classification of the selected light source filter to the light source communication interface section 9 of the endoscope apparatus 2.

Next, specific configurations of the endoscope apparatus 2 and the image server 5 which constitute the medical apparatus of the present embodiment will be described.

As shown in FIG. 1, the endoscope apparatus 2 is a digital imaging apparatus compatible with the DICOM standard, and it is configured to have a scope interface section 6, an image generation section 7, a memory 8, an image processing section 10, a storage section 11, a network interface section 12, and a control section 13. The storage section 3b of the endoscopic scope 3, the scope interface section 6 of the endoscope apparatus 2, the light source communication interface section 9, the control section 13, and the CCU communication interface section 14 of the light source apparatus 4 constitute identification means.

The scope interface section 6 is an interface for detachably and electrically connecting the endoscopic scope 3. When the endoscopic scope 3 is connected to the endoscope apparatus 2, the scope interface section 6 takes in the identification information, such as a scope ID, stored in the storage section 3b of the endoscopic scope 3, processes the identification information by a scope ID processing section 6a, and then outputs the information to the control section 13.

The image generation section 7 takes in an image pickup signal picked up by the CCD 3a of the endoscopic scope 3, performs signal processing, and outputs the signal to the image processing section 10. The memory 8 stores the data, such as an endoscopic image, obtained by the endoscopic scope 3.

The light source communication interface section 9 is an interface for electrically connecting to the CCU communication interface section 14 of the light source apparatus 4 to perform communication. For example, when an operation of selecting a light source filter of the light source apparatus 4 is performed, identification information such as the classification of the selected light source filter is sent from the light source apparatus 4, and the light source communication interface section 9 receives and takes in the sent identification information, and outputs the identification information to the control section 18.

For the image data supplied via the image generation section 7, the image processing section 10 performs processing required to output the image data to a connected display device (not shown) and the image server 5 connected via the network interface section 12.

For example, in the case of outputting the image data to the image server 5 via the network interface section 12, the image processing section 10 performs predetermined processing of the image data so that the image data becomes image data compatible with the DICOM standard under the control of the control section 13.

The network interface section 12 is an interface for electrically connecting to the image server 5 via the network. The network interface section 12 outputs the image data compatible with the DICOM standard, such as an endoscopic image, which has been processed by the image processing section 103 to the image server 5 via the network.

In the present embodiment, there is stored in the storage section 11 of the endoscopic scope 3 information regarding processing to be executed according to the classification of the endoscopic scope 3 constituting the testing apparatus and the classification of the light source filter of the light source apparatus 4.

That is, the information is information corresponding to multiple SOPs specified in the DICOM standard.

Specifically, the storage section 11 has an OS section 11a in which program information such as an OS required, for example, to display DICOM-standard image data to be outputted is stored, and an application section 11b in which information corresponding to the multiple SOPs specified in the DICOM standard is stored.

Figure 2:
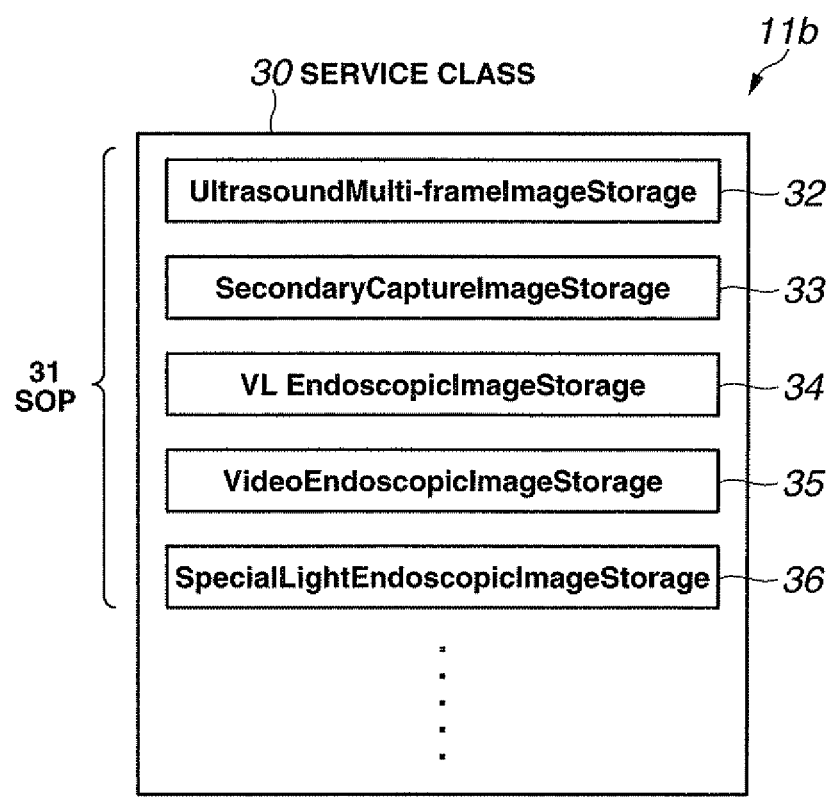
FIG. 2 is a diagram for illustrating multiple SOPs based on the DICOM standard stored in a storage section of the medical apparatus in FIG. 1.

As shown in FIG. 2, the information stored in the application section 11b is, for example, information including a DICOM-standard service class (SERVICE CLASS) 30. The service class 30 is configured to have multiple SOPs 31.

In this case, SOPs 32 to 35 are included in the multiple SOPs 31 as shown in FIG. 2. To describe it in detail, the SOP 32 is, for example, an SOP regarding (Ultrasound Multi-frame Image Storage) as shown in FIG. 2. The SOP is information accompanying processing of ultrasound observation image data by the ultrasound test endoscopic scope 3B.

The SOP 33 is an SOP regarding (Secondary Capture Image Storage), which is information based on processing attaching importance to versatility of being compatible with image data of all digital image apparatuses.

The SOP 34 is an SOP regarding (VL Endoscopic Image Storage), which is information accompanying processing of image data of a still image obtained by an optical endoscopic scope, specifically the visible-light test endoscopic scope 3A.

The SOP 35 is an SOP regarding (Video Endoscopic Image Storage), which is information accompanying processing of image data of a moving image obtained by an optical endoscopic scope, specifically the visible-light test endoseopic scope 3A.

The SOP 36 is an SOP regarding (Special Light Endoscopic Image Storage), which is information accompanying image data processing of endoscopic image data other than the SOPs 32 to 35, for example, image data obtained by the special-light test endoscopic scope 3C or the like.

The SOPs 31 of the service class 30 are not limited to the SOPs 32 to 36 described above. Any SOP may be added if the SOP is a DICOM-standard-based SOP compatible with a medical testing apparatus to be connected. The SOP 33 attaching importance to versatility constitutes the particular information described above. Furthermore, the SOP 36 is not limited to the information described above, and preset information other than the information may be used.

The control section 13 controls the entire medical system 1 and the entire endoscope apparatus 2.

In the present embodiment, the control section 13 identifies the classification of the connected endoscopic scope 3 (specifically, the visible-light test endoscopic scope 3A, the ultrasound test endoscopic scope 3B or the special-light test endoscopic scope 3C) on the basis of the scope ID information from the scope ID processing section 6a. On the basis of the classification as a result of the identification, the control section 13 reads an SOP corresponding to the classification from the SOPs 31 stored in the application section 11b of the storage section 11 and sets the SOP. In the case where the SOP corresponding to the classification does not exist, the control section 13 performs switching control so that the SOP 22, which is predetermined information, is read from the SOPs 31 stored in the application section 11b and set.

Figure 4:
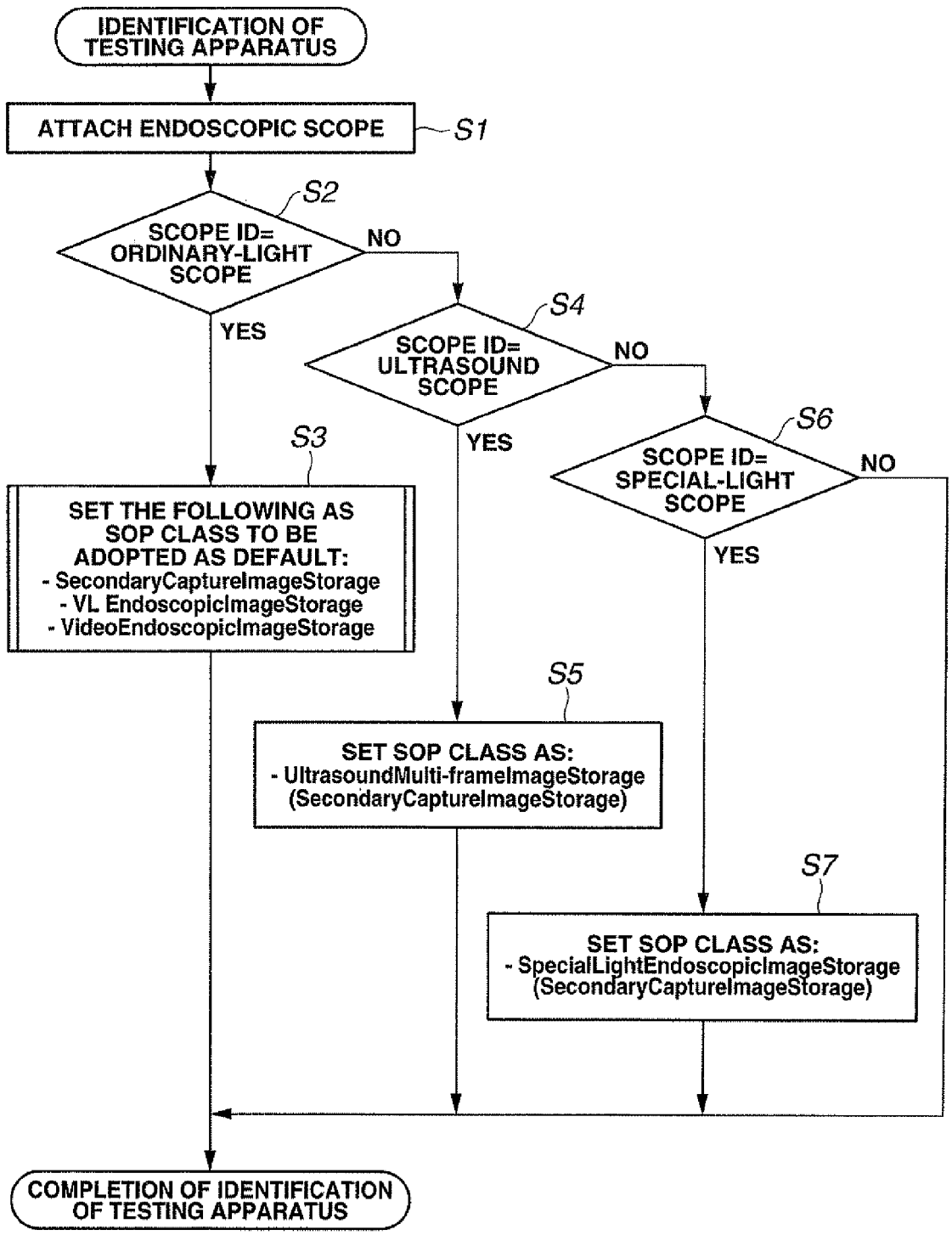
FIG. 4 is a flowchart showing an example of control by a control section to illustrate the operation of the medical apparatus in FIG. 1.

A flowchart showing an example of the control is shown in FIG. 4.

Next, the control operation of the medical system 1 of the present embodiment will be described with reference to FIG. 4.

In the medical system 1 of the present embodiment, when the power source is turned on, the control section 13 of the endoscope apparatus 2 reads and activates a testing apparatus identification program shown in FIG. 4, which is stored in an internal memory not shown.

As shown in FIG. 4, in the control section 13 when any endoscopic scope 3 among the endoscopic scopes 3A to 3C shown in FIG. 3 is selected according to the contents of a test, the connector section 3z of the selected endoscopic scope 3 is inserted into the connector section 2A of the light source apparatus 4, and, at the same time, the endoscopic scope 3 is connected to the endoscope apparatus 2 with the use of a scope not shown, by processing of step S1, the identification information, such as a scope ID, which is stored in the storage section 3b of the connected endoscopic scope 3 is taken in via the scope cable, the scope interface section 6 and the scope ID processing section 6a.

Then, the control section 13 identifies whether or not the scope ID information from the scope ID processing section 6a indicates the visible-light test endoscopic scope 3A, which is an ordinary-light scope, by determination processing of step S2. If the scope ID information indicates the visible-light test endoscopic scope 3A, the control section 13 proceeds to processing of step S3. Otherwise, the control section 13 proceeds to processing of step S4.

When it is identified that the scope ID information indicates the visible-light test endoscopic scope 3A, the control section 13 reads the SOP 33 regarding (Secondary Capture Image Storage), the SOP 34 regarding (VL Endoscopic Image Storage) and the SOP 35 regarding (Video Endoscopic Image Storage) from the application section 11b of the storage section 11 and sets the SOPs 33 to 35 as an SOP class to be adopted as a default, by processing of step S3, and ends the testing apparatus identification program.

In this case, an order of priority may be set among the SOPs 33 to 35, and, for example, the SOP 33 regarding (Secondary Capture Image Storage) may be set to be at the lowest position in the priority ranking.

On the other hand, if identifying that the scope ID information does not indicate the visible-light test endoscopic scope 3A, the control section 13 identifies whether or not the scope ID information indicates the ultrasound test endoscopic scope 3B by determination processing of step S4. If the scope ID information indicates the ultrasound test endoscopic scope 3B, the control section 13 proceeds to processing of step S5. Otherwise, the control section 13 proceeds to step 86.

If identifying that the scope ID information indicates the ultrasound test endoscopic scope 3B, the control section 13 reads the SOP 32 regarding (Ultrasound Multi-frame Image Storage) and the SOP 33 regarding (Secondary Capture Image Storage) from the application section 11b of the storage section 11 and sets the SOPs 32 and 33 as an SOP class to be adopted, by processing of step S5, and ends the testing apparatus identification program.

In this case, an order of priority may be set between the SOP 32 and 33, and, for example, the SOP 33 regarding (Secondary Capture Image Storage) may be set to be the lowest position in the priority ranking.

On the other hand, if identifying that the scope ID information does not indicate the ultrasound test endoscopic scope 3B, the control section 13 identifies whether or not the scope ID information indicates the special-light test endoscopic scope 3C by determination processing of step S6. If the scope ID information indicates the special-light test endoscopic scope 3C, the control section 13 proceeds to processing of step S7. Otherwise, the control section 13 ends the testing apparatus identification program.

If identifying that the scope ID information indicates the special-light test endoscopic scope 3C, the control section 13 reads the SOP 36 regarding (Special Light Endoscopic Image Storage) and the SOP 33 regarding (Secondary Capture Image Storage) from the application section 11b of the storage section 11 by the processing of step S6, sets the SOPs 36 and 33 as an SOP class to be adopted, and ends the testing apparatus identification program.

In this case, an order or priority may be set between the SOPs 36 and 33, and, for example, the SOP 33 regarding (Secondary Capture Image Storage) may be set to be at the lowest position in the priority ranking.

Thus, by the testing apparatus identification program being executed, an SOP for performing optimum processing is automatically set according to the classification of the endoscopic scope 3 connected to the endoscope apparatus 2.

The control section 13 is adapted to set the SOP 33 regarding (Secondary Capture Image Storage) having versatility, which is stored in the application section 11b of the storage section 1, in the case where the result of the classification of the endoscopic scope 3 does not correspond to any endoscopic scopes 3.

Thereafter, the control section 13 performs predetermined processing of supplied image data on the basis of the set SOPs 31 so that the image data becomes image data compatible with the DICOM standard, with the use of the image processing section 10. Then, the control section 13 supplies the DICOM-standard-applied image data which has been generated by the image processing section 10 to the network interface section 12, and outputs the image data to the image server 5 via the network.

Thus, according to the first embodiment, by selecting an SOP to be applied to test processing by the endoscopic scope 3 on the basis of the result of identification from setting information stored in advance, on the basis of the result of identification of the endoscopic scope 3, which is a testing apparatus, and setting the SOP, it is possible to output optimum image data compatible with the DICOM standard to the image server 5.

<Second Embodiment>

In a second embodiment, the medical testing apparatus is the light source apparatus 4 having information regarding a light source filter, and the control section 13 identifies the classification of the light source filter on the basis of the information regarding the light source filter of the light source apparatus 4 and performs control so that an optimum SOP is set.

The entire configuration of the medical system 1 of the second embodiment is substantially the same as that of the first embodiment, but the control by the control section 13 of the endoscope apparatus 2 is different.

Figure 5:
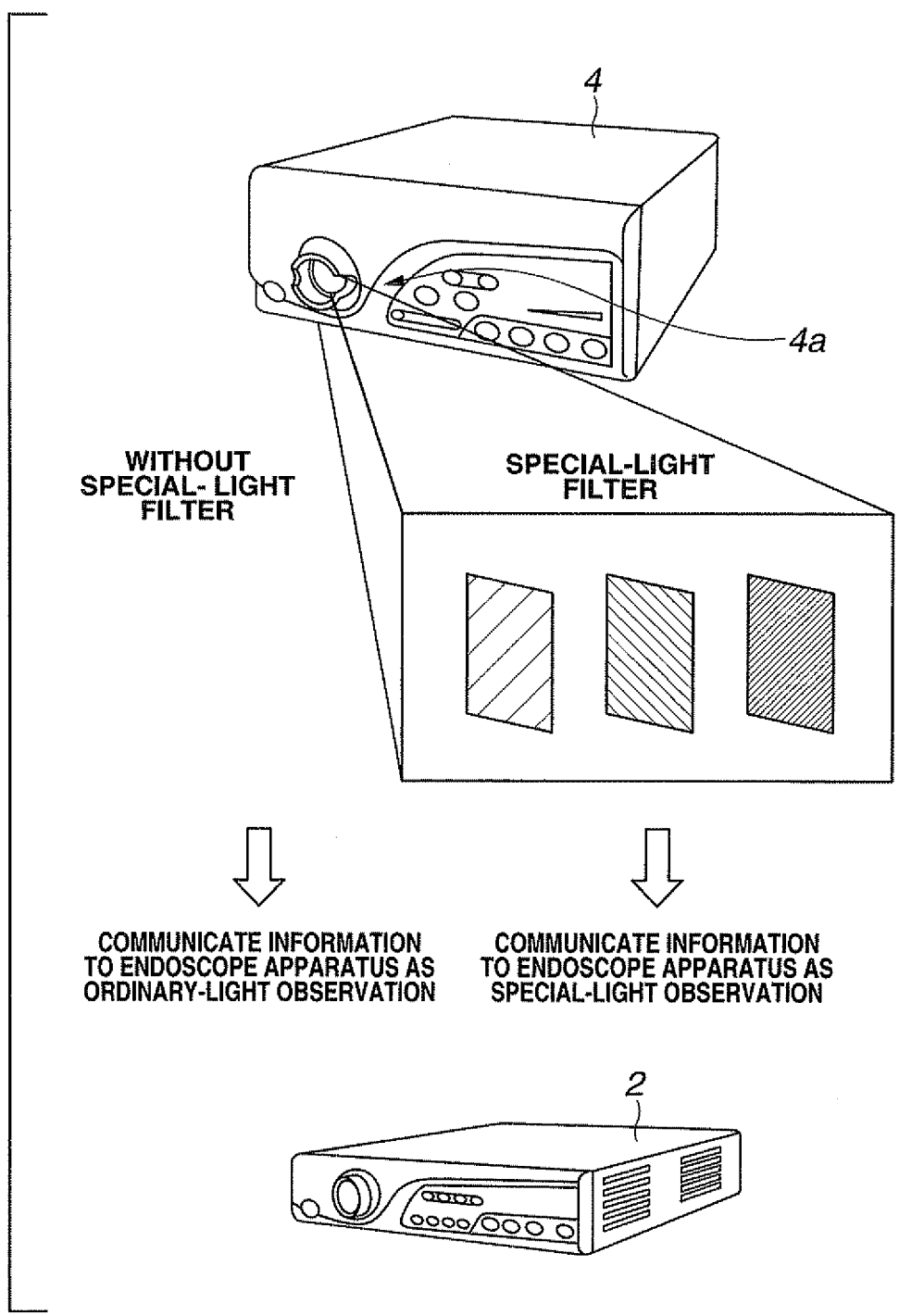
FIG. 5 is a diagram showing that, when a light source filter of a light source apparatus is selected, identification information of the light source filter is supplied to an endoscope apparatus, according to a second embodiment of the present invention.

That is, in the second embodiment, the control section 13 identifies the classification of a selected light source filter of the light source apparatus 4 (specifically, not using a light source filter in the case where ordinary light is selected, using a special-light light source filter in the case where not ordinary light but special light is selected, and the like; see FIG. 5) on the basis of identification information, such as the classification of the light source filter, which is obtained by communication with the CCU communication interface section 14 of the light source apparatus 4. The control section 13 reads an SOP corresponding to the classification from the SOPs 31 stored in the application section 11*b* of the storage section 11, on the basis of the classification as a result of the identification. In the case where the SOP corresponding to the classification does not exist, the control section 13 performs switching control so that the SOP 22, which is predetermined information, is read from the SOPs 31 stored in the application section 11*b* and set.

Figure 6:
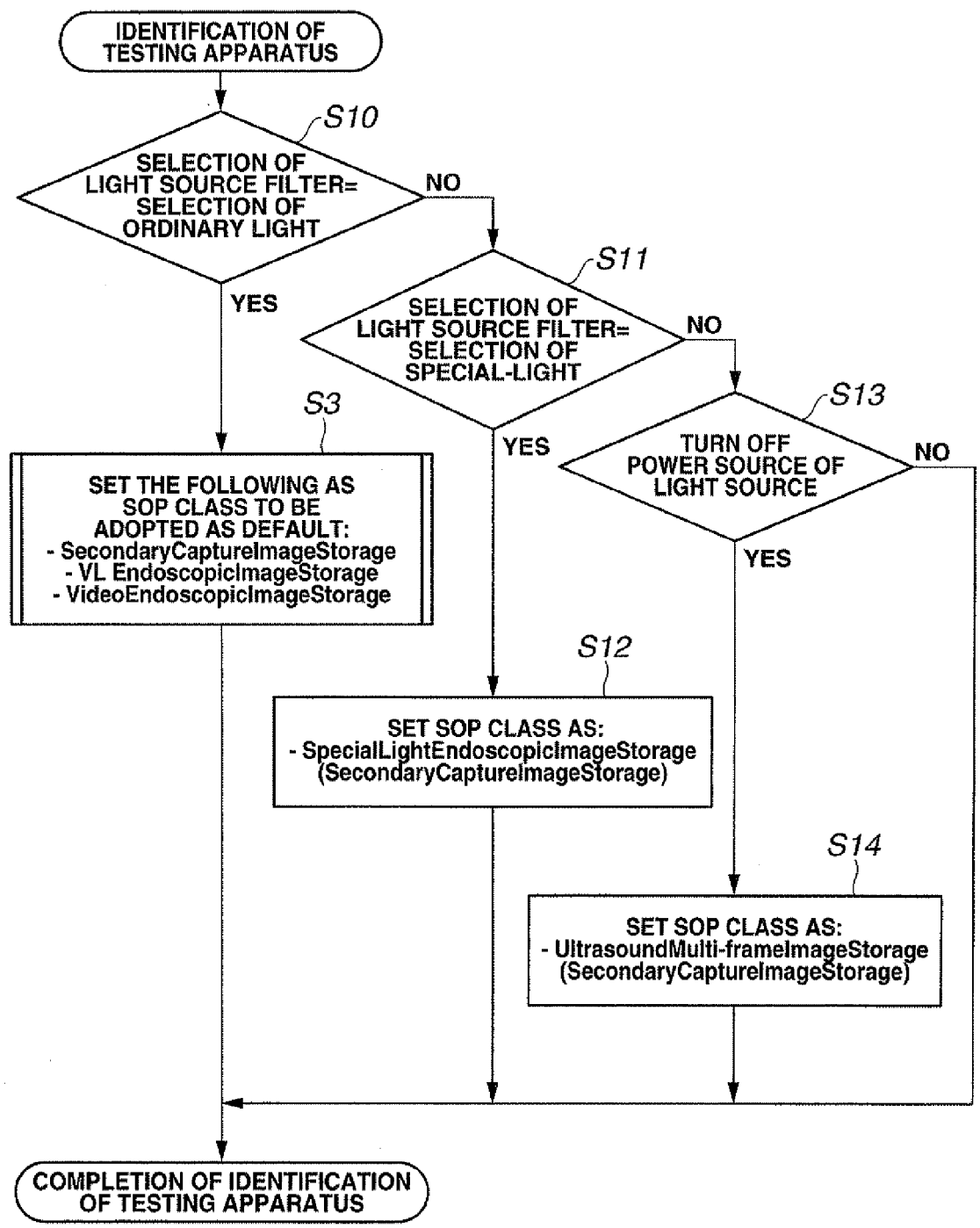
FIG. 6 is a flowchart showing an example of control by a control section to illustrate the operation of a medical apparatus of the second embodiment.

A flowchart showing an example of the control is shown in FIG. 6.

Next, the control operation of the medical system of the present embodiment will be described with reference to FIG. 6.

In the medical system 1 of the present embodiment, when the power source is turned on, the control section 13 of the endoscope apparatus 2 reads and activates a testing apparatus identification program shown in FIG. 6, which is stored in the internal memory not shown.

As shown in FIG. 6, when a light source filter of the light source apparatus 4 shown in FIG. 5 is selected according to the contents of a test by processing of step S10, the control section 13 takes in identification information such as the classification of the selected light source filter by communication with the CCU communication interface section 14 of the light source apparatus 4 via the light source communication interface section 9.

Then, the control section 13 identifies whether or not the taken in identification information indicates that ordinary light is selected and a light source filter is not to be used. If the identification information indicates so, the control section 13 proceeds to processing of step S3. Otherwise, the control section 13 proceeds to processing of step S1.

When identifying that the identification information indicates that ordinary light is selected and a light source filter is not to be used, the control section 13 reads the SOP 33 regarding (Secondary Capture Image Storage), the SOP 34 regarding (VL Endoscopic Image Storage) and the SOP 35 regarding (Video Endoscopic Image Storage) from the application section 11*b* of the storage section 11 and sets the SOPs 33 to 35 as an SOP class to be adopted as a default, by processing of step S3, and ends the testing apparatus identification program.

In this case, an order of priority may be set among the SOPs 33 to 35, and, for example, the SOP 33 regarding (Secondary Capture Image Storage) may be set to be at the lowest position in the priority ranking.

On the other hand, if identifying that the identification information is not the identification information indicating that ordinary light is selected and a light source filter is not to be used, the control section 13 identifies whether or not the identification information indicates a special-light light source filter which is used when special light is selected by determination processing of step S11. If the identification information indicates the special-light light source filter, the control section 13 proceeds to processing of step S12. Otherwise, the control section 13 proceeds to step S13.

When identifying that the identification information indicates the special-light light source filter, the control section 13 reads the SOP 36 regarding (Special Light Endoscopic Image Storage) and the SOP 33 regarding (Secondary Capture Image Storage) from the application section 11*b* of the storage section 1 and sets the SOPs 36 and 33 as an SOP class to be adopted by processing of step S12, and ends the testing apparatus identification program.

In this case, an order of priority may be set between the SOPs 36 and 33, and, for example, the SOP 33 regarding (Secondary Capture Image Storage) may be set to be at the lowest position in the priority ranking.

On the other hand, if identifying that the identification information does not indicate the special-light light source filter, the control section 13 judges whether or not the power source of the light source apparatus 4 is off, by determination processing of step 813. If the power source is oft the control section 13 proceeds to processing of step S14. Otherwise, the control section 13 ends the testing apparatus identification program.

If determining that the power source of the light source apparatus 4 is off, the control section 13 reads the SOP 32 regarding (Ultrasound Multi-frame Image Storage) and the SOP 33 regarding (Secondary Capture Image Storage) from the application section 11*b* of the storage section 11 and sets the SOPs 32 and 33 as an SOP class to be adopted, by processing of step S14, and ends the testing apparatus identification program.

In this case, an order of priority may be set between the SOPs 32 and 33, and, for example, the SOP 33 regarding (Secondary Capture Image Storage) may be set to be at the lowest position in the priority ranking.

Thus, by the testing apparatus identification program being executed, an SOP for performing optimum processing is automatically set according to the classification of the light source filter of the light source apparatus 4 connected to the endoscope apparatus 2.

The control section 13 is adapted to set the SOP 33 regarding (Secondary Capture Image Storage) having versatility, which is stored in the application section 11*b* of the storage section 11, in the case where the result of the classification of the light source filter of the light source apparatus 4 does not correspond to any light source filter.

Thereafter, the control section 13 performs predetermined processing of supplied image data on the basis of the set SOP 31 so that the image data becomes image data compatible with the DICOM standard, with the use of the image processing section 10, similarly to the first embodiment. Then, the control section 13 supplies the DICOM-standard-applied image data which has been generated by the image processing section 10 to the network interface section 12, and outputs the image data to the image server 5 via the network.

Thus, according to the second embodiment, by selecting an SOP to be applied to test processing by the light source filter of the light source apparatus 4 from setting information stored in advance, on the basis of the result of identification of the light source filter of the light source apparatus 4, which is a testing apparatus and setting the SOP, it is possible to output optimum image data compatible with the DICOM standard to the image server 5. Other advantages are similar to those of the first embodiment.

In the first and second embodiments described above, description has been made on the cases in which the endoscopic scope 3 and the light source filter of the light source apparatus 4 are used, respectively, as a medical testing apparatus. However, in cases where medical testing apparatuses other than the endoscopic scope 3 and the light source filter of the light source apparatus 4, similar operations and advantages can be also obtained.

It is apparent that, in the present invention, different embodiments can be configured in a wide range on the basis of the present invention without departing from the spirit and the scope of the present invention. The present invention is only limited by the accompanying claims, and it is not restricted by any particular embodiment thereof.

What is claimed is:

1. A medical apparatus comprising:
   an identification section which identifies the classification of a medical testing apparatus configured to be attachable to and detachable from an endoscope apparatus;
   a storage section which stores information, which corresponds to multiple Service Object Pairs (SOPs) specified in a Digital Imaging and Communications in Medicine (DICOM) standard, regarding processing to be executed according to the classification of the medical testing apparatus, wherein two or more SOPs having an order of priority are set according to the classification of the medical testing apparatus, and the respective SOPs are information for processing of a still image or a moving image obtained by the medical testing apparatus; and
   a control section which reads, on the basis of the classification of the medical testing apparatus obtained by the identification section, information corresponding to the classification from the information stored in the storage section and sets the read information as a Service Object Pair (SOP) class to be adopted according to the order of priority, and, in the case where the information corresponding to the classification does not exist, reads predetermined information from the information stored in the storage section, sets the read predetermined information as an SOP class to be adopted, generates an image processed so as to become compatible with the DICOM standard based on the set SOP class, and outputs data of the generated image compatible with the DICOM standard.

2. The medical apparatus according to claim 1, wherein
   the medical testing apparatus is an endoscope which is attachable and detachable and which has scope ID information for classification; and
   the identification section identifies the classification of the medical testing apparatus on the basis of the scope ID information of the endoscope.

3. The medical apparatus according to claim 1, wherein
   the medical testing apparatus is a light source apparatus having information regarding a light source filter; and
   the identification section identifies the classification of the medical testing apparatus on the basis of the information regarding the light source filter of the light source apparatus.

4. A medical system comprising:
   a medical apparatus comprising:
   a medical testing apparatus configured to be attachable to and detachable from an endoscope apparatus;
   an identification section which identifies the classification of the medical testing apparatus;
   a storage section which stores information, which corresponds to multiple Service Object Pairs (SOPs) specified in a Digital Imaging and Communications in Medicine (DICOM) standard, regarding processing to be executed according to the classification of the medical testing apparatus, the respective SOPs are information for processing of a still image or a moving image obtained by the medical testing apparatus; and
   a control section which reads, on the basis of the classification of the medical testing apparatus obtained by the identification section, information corresponding to the classification from the information stored in the storage section and sets the read information as an SOP class to be adopted according to the order of priority, and, in the case where the information corresponding to the classification does not exist, reads predetermined information from the information stored in the storage section, sets the predetermined information as an SOP class to be adopted, generates an image processed so as to become compatible with the DICOM standard based on the set SOP class, and outputs data of the generated image compatible with the DICOM standard; and
   a medical server capable of sending and receiving the data of the image to and from the medical apparatus by connecting the medical apparatus via a network.

5. The medical system according to claim 4, wherein
   the medical testing apparatus is an endoscope which is attachable and detachable and which has scope ID information for classification; and
   the identification section of the medical apparatus identifies the classification of the medical testing apparatus on the basis of the scope ID information of the endoscope.

6. The medical system according to claim 4, wherein
   the medical testing apparatus is a light source apparatus having information regarding a light source filter; and
   the identification section of the medical apparatus identifies the classification of the medical testing apparatus on the basis of the information regarding the light source filter of the light source apparatus.

* * * * *

UNITED STATES PATENT AND TRADEMARK OFFICE
CERTIFICATE OF CORRECTION

| | | |
|---|---|---|
| PATENT NO. | : 8,915,838 B2 | Page 1 of 1 |
| APPLICATION NO. | : 12/184823 | |
| DATED | : December 23, 2014 | |
| INVENTOR(S) | : Takashi Ozaki | |

It is certified that error appears in the above-identified patent and that said Letters Patent is hereby corrected as shown below:

On the Title Page, Item (73)

It Should Read:

Assignee: Olympus Medical Systems Corp., Tokyo (JP)

Signed and Sealed this
Seventh Day of July, 2015

Michelle K. Lee
*Director of the United States Patent and Trademark Office*